US012365720B2

(12) United States Patent
Alcami Pertejo et al.

(10) Patent No.: US 12,365,720 B2
(45) Date of Patent: Jul. 22, 2025

(54) ETANERCEPT VARIANTS WITH IMPROVED THERAPEUTICAL EFFECT

(71) Applicant: CONSEJO SUPERIOR DE INVESTIGACIONES CIENTÍFICAS, Madrid (ES)

(72) Inventors: Antonio Alcami Pertejo, Madrid (ES); Sergio Martín Pontejo, Madrid (ES); Carolina Sánchez Fernández, Madrid (ES)

(73) Assignee: CONSEJO SUPERIOR DE INVESTIGACIONES CIENTIFICAS, Madrid (ES)

( * ) Notice: Subject to any disclaimer, the term of this patent is extended or adjusted under 35 U.S.C. 154(b) by 876 days.

(21) Appl. No.: 17/294,582

(22) PCT Filed: Oct. 29, 2019

(86) PCT No.: PCT/EP2019/079492
§ 371 (c)(1),
(2) Date: May 17, 2021

(87) PCT Pub. No.: WO2020/099119
PCT Pub. Date: May 22, 2020

(65) Prior Publication Data

US 2022/0002380 A1 Jan. 6, 2022

(30) Foreign Application Priority Data

Nov. 16, 2018 (EP) .................................... 18382812

(51) Int. Cl.
*C07K 14/00* (2006.01)
*A61K 39/00* (2006.01)
*C07K 14/705* (2006.01)
*A61K 38/00* (2006.01)

(52) U.S. Cl.
CPC ................. *C07K 14/70578* (2013.01); *A61K 39/001138* (2018.08); *A61K 38/00* (2013.01)

(58) Field of Classification Search
CPC .......... C07K 14/70578; C07K 2319/30; A61K 39/001138; A61K 38/00
See application file for complete search history.

(56) References Cited

U.S. PATENT DOCUMENTS 5,447,851 A 9/1995 Beutler et al.
5,605,690 A 2/1997 Jacobs et al.
7,923,011 B2 * 4/2011 Adams ...................... A61P 1/00
424/134.1

OTHER PUBLICATIONS

Calmon-Hamaty et al, Arthritis Research and therapy 2011 13: 232 (Year: 2011).*

Wallis et al., "Granulomatous infectious diseases associated with tumor necrosis factor antagonists", Clinical Infectious Diseases, Infectious Diseases Society of America, 2004, vol. 38, pp. 1261-1265, 5 pages.

Yang et al., "The I-TASSER Suite: protein structure and function prediction", Nature America, Inc., 2015, vol. 12, Issue 1, pp. 7-8, 5 pages.

Saraiva and Alcami, "CrmE, a Novel Soluble Tumor Necrosis Factor Receptor Encoded by Poxviruses", American Society for Microbiology, Journal of Virology, 2001, vol. 75, Issue 1, pp. 226-233, 13 pages.

Montanuy et al., "Glycosaminoglycans mediate retention of the poxvirus type I interferon binding protein at the cell surface to locally block interferon antiviral responses", The FASEB Journal, 2011, vol. 25, Issue 6, 12 pages.

Pontejo et al., "Comparative Biochemical and Functional Analysis of Viral and Human Secreted Tumor Necrosis Factor (TNF) Decoy Receptors", The Journal of Biological Chemistry, 2015, vol. 290, Issue 26, pp. 15973-15984, 12 pages.

Murray & Dahl, "Recombinant Human Tumor Necrosis Factor Receptor (P75) Fc Fusion Protein (Tnfr. Fc) in Rheumatoid Arthritis", Annals of Pharmacotherapy, 1997, vol. 31, Issue 11, pp. 1335-1338.

Willrich et al., "Tumor necrosis factor inhibitors: clinical utility in autoimmune diseases", Elsevier, Translation Research, 2015, vol. 165, Issue 2, pp. 270-282.

Shen et al., "T0001, a variant of TNFR2-Fc fusion protein, exhibits improved Fc effector functions through increased binding to membranebound TNFα", PLOS One, 2017, vol. 12, Issue 5, 15 pages.

Pontejo et al., "Insights into ligand binding by a viral tumor necrosis factor (TNF) decoy receptor yield a selective soluble human type 2 TNF receptor", Journal of Biological Chemistry, 2019, vol. 294, Issue 13, pp. 5214-5227, 14 pages.

Haraoui and Bykerk, "Etanercept in the treatment of rheumatoid arthritis", Therapeutics and Clinical Risk Management, Dove Medical Press Limited, 2007, vol. 3, Issue 1, pp. 99-105, 8 pages.

Mitoma et al., "Molecular mechanisms of action of anti-TNF-a agents—Comparison among therapeutic TNF-α antagonists", Cytokine, Elsevier, 2016, vol. 101, 8 pages.

Roach et al., "Secreted Lymphotoxin-α Is Essential for the Control of an Intracellular Bacterial Infection", Journal of Experimental Medicine, 2001, vol. 193, Issue 2, pp. 239-246, 8 pages.

(Continued)

*Primary Examiner* — Lei Yao
(74) *Attorney, Agent, or Firm* — Hayes Soloway PC

(57) ABSTRACT

The present invention provides improved Etanercept variants which comprise one (A105E), preferably two (A105E/L106F), amino acid substitutions regarding the Etanercept original amino acid sequence of SEQ ID NO: 3. These variants inhibit TNF activity but fail to neutralize human LTα (hLTα). Thus, they are proposed herein as a great alternative to be used in the clinic for the treatment of autoimmune or inflammatory diseases in which an exacerbated TNF activity is involved, since they prevent the side effects associated to the use of the original Etanercept molecule while retaining the TNF blocking activity.

11 Claims, 2 Drawing Sheets

Specification includes a Sequence Listing.

(56) References Cited

OTHER PUBLICATIONS

Ehlers et al., "The Lymphotoxin β Receptor Is Critically Involved in Controlling Infections with the Intracellular Pathogens *Mycobacterium tuberculosis* and Listeria monocytogenes", The Journal of Immunology, 2003, vol. 170, Issue 10, pp. 5210-5218, 9 pages.
Bopst et al., "Differential effects of TNF and LT in the host defense against M. bovis BCG", European Journal of Immunology, 2001, vol. 31, pp. 1935-1943, 18 pages.

* cited by examiner

SEQUENCE LISTING

```
<160> NUMBER OF SEQ ID NOS: 12

<210> SEQ ID NO 1
<211> LENGTH: 235
<212> TYPE: PRT
<213> ORGANISM: Artificial Sequence
<220> FEATURE:
<223> OTHER INFORMATION: Ligand binding domain of the human TNF receptor
      2 (TNFR2)

<400> SEQUENCE: 1

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125
```

-continued

```
Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp
225                 230                 235


<210> SEQ ID NO 2
<211> LENGTH: 235
<212> TYPE: PRT
<213> ORGANISM: Artificial Sequence
<220> FEATURE:
<223> OTHER INFORMATION: SEQ ID NO: 1 comprising the amino acid
      substitutions A105E and L106F

<400> SEQUENCE: 2

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Glu Phe Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp
225                 230                 235


<210> SEQ ID NO 3
```

-continued

<211> LENGTH: 467
<212> TYPE: PRT
<213> ORGANISM: Artificial Sequence
<220> FEATURE:
<223> OTHER INFORMATION: Etanercept original sequence

<400> SEQUENCE: 3

```
Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380
```

```
Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465


<210> SEQ ID NO 4
<211> LENGTH: 467
<212> TYPE: PRT
<213> ORGANISM: Artificial Sequence
<220> FEATURE:
<223> OTHER INFORMATION: SEQ ID NO: 1 comprising the amino acid
      substitutions A105E and L106F (i. e. SEQ ID NO: 2) linked to the
      Fc fragment of a human IgG1 shown in SEQ ID N: 11

<400> SEQUENCE: 4

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Glu Phe Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Glu Pro Lys Ser Cys
225                 230                 235                 240

Asp Lys Thr His Thr Cys Pro Pro Cys Pro Ala Pro Glu Leu Leu Gly
                245                 250                 255
```

-continued

```
Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465


<210> SEQ ID NO 5
<211> LENGTH: 36
<212> TYPE: DNA
<213> ORGANISM: Artificial Sequence
<220> FEATURE:
<223> OTHER INFORMATION: Primer Crm34

<400> SEQUENCE: 5

gcgggatccg atgttccgta tacacccatt aatggg                                36


<210> SEQ ID NO 6
<211> LENGTH: 32
<212> TYPE: DNA
<213> ORGANISM: Artificial Sequence
<220> FEATURE:
<223> OTHER INFORMATION: Primer CrmD33

<400> SEQUENCE: 6

gcgctcgagg catctctttc acaatcattt gg                                    32


<210> SEQ ID NO 7
<211> LENGTH: 31
<212> TYPE: DNA
<213> ORGANISM: Artificial Sequence
<220> FEATURE:
<223> OTHER INFORMATION: Primer RM6mut2F

<400> SEQUENCE: 7

gctggtactg cgcgttcagc aagcaggagg g                                     31
```

-continued

<210> SEQ ID NO 8
<211> LENGTH: 31
<212> TYPE: DNA
<213> ORGANISM: Artificial Sequence
<220> FEATURE:
<223> OTHER INFORMATION: Primer RM6mut2R

<400> SEQUENCE: 8
ccctcctgct tgctgaacgc gcagtaccag c 31

<210> SEQ ID NO 9
<211> LENGTH: 33
<212> TYPE: DNA
<213> ORGANISM: Artificial Sequence
<220> FEATURE:
<223> OTHER INFORMATION: Primer RM6mut3F

<400> SEQUENCE: 9
cggctggtac tgcgagttca gcaagcagga ggg 33

<210> SEQ ID NO 10
<211> LENGTH: 33
<212> TYPE: DNA
<213> ORGANISM: Artificial Sequence
<220> FEATURE:
<223> OTHER INFORMATION: Primer RM6mut3R

<400> SEQUENCE: 10
ccctcctgct tgctgaactc gcagtaccag ccg 33

<210> SEQ ID NO 11
<211> LENGTH: 232
<212> TYPE: PRT
<213> ORGANISM: Artificial Sequence
<220> FEATURE:
<223> OTHER INFORMATION: Fc fragment of a human IgG1

<400> SEQUENCE: 11

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
```

-continued

```
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230


<210> SEQ ID NO 12
<211> LENGTH: 22
<212> TYPE: PRT
<213> ORGANISM: Artificial Sequence
<220> FEATURE:
<223> OTHER INFORMATION: Signal peptide

<400> SEQUENCE: 12

Met Ala Pro Val Ala Val Trp Ala Ala Leu Ala Val Gly Leu Glu Leu
1               5                   10                  15

Trp Ala Ala Ala His Ala
            20
```

ETANERCEPT VARIANTS WITH IMPROVED THERAPEUTICAL EFFECT

CROSS-REFERENCE TO RELATED APPLICATIONS AND PRIORITY

This patent application claims priority from PCT Patent Application No. PCT/EP2019/079492 filed Oct. 29, 2019, which claims priority from European Patent Application No. 18382812.8 filed Nov. 16, 2018. Each of these patent applications are herein incorporated by reference in their entirety.

The invention belongs to the field of medicine and pharmacology, specifically to therapeutic chimeric fusion proteins that bind human tumor necrosis factor (hTNF) and inhibit its biological effect in inflammation processes. These fusion proteins are therefore useful for treating autoimmune and/or inflammatory diseases in which TNF is involved. In particular, this invention refers to mutant variants of the fusion protein Etanercept that improve its TNF neutralizing specificity and therefore its therapeutical effect. These improved mutants specifically inhibit hTNF, retaining thus the anti-inflammatory therapeutic effect of the original compound, while they display a highly reduced capacity to block human lymphotoxin (hLT) and therefore ameliorate the side effects associated to the clinical use of Etanercept.

BACKGROUND ART

The tumor necrosis factor superfamily (TNFSF) comprises 19 cytokines and 29 cellular receptors involved in essential biological processes such as cell death, immunity and organ development. However, a deregulated production of these cytokines can provoke autoimmunity and inflammatory disorders. For instance, Crohn's disease, psoriasis, ankylosing spondylitis, rheumatoid arthritis and inflammatory bowel disease are often associated with the uncontrolled activity of tumor necrosis factor α (TNF), the archetypical cytokine of the family.

Up to date, there are five TNF inhibitors approved by the Food and Drug Administration (FDA) for the treatment of these diseases: four monoclonal antibodies (infliximab, adalimumab, certolizumab, and golimumab) and a soluble decoy receptor, Etanercept also called Enbrel (Willrich, M. A. V., et al., 2015, Transl Res 165, 270-282). Etanercept is a chimeric fusion protein of the ligand binding domain of the cellular TNF receptor 2 (TNFR2) with the Fc portion of a human IgG1 (Murray, K. M., Dahl, S. L., 1997, Ann Pharmacother 31, 1335-1338). Etanercept is thus a biological medical product that treats autoimmune and inflammatory diseases by interfering with the soluble inflammatory cytokine TNF. It binds TNF and decreases its role in disorders involving excess of inflammation in humans and other animals, including autoimmune diseases such as ankylosing spondylitis, juvenile rheumatoid arthritis, plaque psoriasis, psoriatic arthritis, rheumatoid arthritis, and, potentially, in a variety of other disorders mediated by a TNF excess. Consequently, it has been approved to treat these diseases. TNF is the "master regulator" of the inflammatory (immune) response in many organ systems. Autoimmune diseases are caused by an overactive immune response. Etanercept has therefore the potential to treat these diseases by inhibiting TNF. This fusion protein was patented in U.S. Pat. No. 5,447,851B1.

Furthermore, U.S. Pat. No. 5,605,690 discloses a method for treating TNF-dependent inflammatory diseases, such as arthritis, by administering a TNF antagonist, such as soluble human TNFR to a human.

Some biosimilars of Etanercept have been developed under the trade names "Etacept" (Cipla), "Benepali" (Samsung Bioepis) or "Erelzi" (Sandoz).

Nevertheless, despite its proved efficiency in ameliorating patient symptomatology, Etanercept can also cause major adverse effects including increased susceptibility to viral or fungal infections such as herpes or Candida, or increased risk of developing tuberculosis or hepatitis B, lymphoma or other types of cancer, multiple sclerosis, convulsions, heart failure, lupus, psoriasis, or autoimmune hepatitis (Fellermann, K., 2013, Dig Dis 31, 374-378). Serious infections and sepsis, including fatalities, have been reported with the use of Etanercept including reactivation of latent tuberculosis and hepatitis B infections. On May 2, 2008, the FDA placed a black box warning on Etanercept due to a number of serious infections associated with the drug.

These side effects might be explained, at least in part, by the fact that Etanercept blocks not only TNF but also other TNFSF ligands essential for homeostasis and immunity like lymphotoxin α (LTα) (Mitoma, H., et al., 2018, Cytokine 101, 56-63). Several reports have shown that LTα is important for host defense against *Mycobacterium* infections (Roach, D. R., Briscoe, H., Saunders, B., et al., 2001, J. Exp. Med. 193, 239-246; Ehlers, S., Holscher, C., Scheu, S., et al., 2003, J. Immunol. 170, 5210-5218), which constitutes one of the major infectious complications in patients under anti-TNF therapy. Importantly, the LTα activity is more markedly decisive in these infections in the absence of TNF (Bopst, M., Garica, I., Guler R., et al., 2001, Eur. J. Immunol. 31, 1935-1943), what simulates the undergoing immunological condition in these patients. Therefore, the anti-LTα activity of this drug may contribute to aggravate the infections in patients treated with Etanercept.

A more specific anti-TNF treatment can be achieved with any of the approved TNF monoclonal antibodies mentioned above. However, it has been reported that the risk of infection associated with these antibodies can be even higher than with Etanercept (Wallis, R. S., Broder M. S., Wong J., et al., 2004, Clin. Infect. Dis. 38, 1261-1265). This might be explained by the potent cytotoxic activities mediated by the Fc region of these antibodies, which may result in the destruction of TNF-bearing immune cells (Mitoma, H., et al., 2018, Cytokine 101, 56-63).

Thus, for the reasons stated above, redesign and improvement of the Etanercept molecule appears to be desirable for achieving a safer application of this drug in the clinic.

There remains a need for a new and improved pharmacologic treatment of autoimmune and inflammatory diseases with Etanercept as a TNF antagonist or TNF blocker, which is greatly beneficial for the large number of patients whom these conditions affect and which avoids the undesirable side effects derived from the Etanercept administration.

DESCRIPTION OF THE INVENTION

The present invention provides improved Etanercept variants which comprise one (A105E), preferably two (A105E/L106F), amino acid substitutions regarding the Etanercept original amino acid sequence of SEQ ID NO: 3. These variants inhibit TNF activity but do not neutralize efficiently human LTα (hLTα). Thus, they are proposed herein as a great alternative to be used in the clinic, since they prevent the side effects associated to the use of the original Etanercept molecule while retaining the TNF blocking activity.

Inventors have identified the amino acid residues that prevent a soluble viral TNF decoy receptor (CrmD) from blocking hLTα (FIG. 1) and successfully transferred these into the Etanercept sequence to specifically hamper its anti-LTα activity (FIGS. 2A-2B). Resultant Etanercept variants disclosed herein have specificity for hTNF and a highly reduced ability to block hLTα, having thus the potential to be used in the clinic as a safer alternative to Etanercept.

In this application it is demonstrated that the anti-hLTα activity of Etanercept can be vastly hampered by making its 90 s loop look more like that of CrmD in A105E and A105E/L106F Etanercept mutants. Therefore, Etanercept variants disclosed in this invention are proposed as a safer second generation of Etanercept, featuring the benefits of a soluble decoy receptor and the high TNF specificity of the antibody therapy overcoming the side effects of the original drugs.

Since the variants disclosed in this invention are mutants of a compound (Etanercept) extensively used and approved in the clinic, they can be administered to the patient in a reliable and safe way.

A first aspect of the invention refers to an isolated polypeptide, hereinafter the "polypeptide of the invention", "variant of the invention" or "mutant of the invention", comprising the amino acid sequence of SEQ ID NO: 1, wherein said amino acid sequence of SEQ ID NO: 1 comprises the amino acid substitution A105E.

In a preferred embodiment the polypeptide of the invention further comprises the amino acid substitution L106F.

Positions 105 and 106 referred to in the present invention relates to positions in the entire sequence of SEQ ID NO: 1, wherein SEQ ID NO: 1 is the amino acid sequence of the ligand binding domain of the human TNF receptor 2 (TNFR2).

Positions 105 and 106 of SEQ ID NO: 1 correspond also with positions 105 and 106 of SEQ ID NO: 3, wherein SEQ ID NO: 3 is the amino acid sequence of the non-mutated, original or wild-type Etanercept, since original Etanercept shown in SEQ ID NO: 3 is a fusion protein comprising the ligand binding domain of TNFR2 shown in SEQ ID NO: 1 linked to the Fc region of a human IgG1 shown in SEQ ID NO: 11.

In the most preferred embodiment, the polypeptide of the invention comprises the amino acid substitutions A105E and L106F. The polypeptide of the invention comprising the amino acid sequence of SEQ ID NO: 1 wherein said amino acid sequence of SEQ ID NO: 1 comprises the amino acid substitutions A105E and L106F is preferably the polypeptide of SEQ ID NO: 2.

In another preferred embodiment, the polypeptide of the invention is linked to the Fc fragment of a human IgG1. More preferably, the Fc fragment of a human IgG1 is that shown in SEQ ID NO: 11.

Even more preferably, the polypeptide of the invention comprises, even more preferably consists of, the amino acid sequence of SEQ ID NO: 4. SEQ ID NO: 4 is the SEQ ID NO: 1 comprising the amino acid substitutions A105E and L106F (i. e. SEQ ID NO: 2) linked to the Fc fragment of a human IgG1 shown in SEQ ID NO: 11.

The term "variant", as used herein, relates to a fusion protein or fusion polypeptide that derives from the Etanercept original sequence (shown in SEQ ID NO: 3) by means of one or more substitutions of one or more amino acids, preferably one, more preferably two amino acids substitutions, at the positions described herein within its amino acid sequence and, therefore, it has a different sequence to that of the original or wild-type fusion protein. As used herein, the expression "Etanercept variant" or "Etanercept mutant" means a polypeptide having hTNF blocking activity and reduced anti-hLTα activity compared with the original Etanercept molecule and which has been produced by chemical synthesis or recombinantly by an organism or cell that expresses a nucleotide sequence that encodes the polypeptide of the invention described herein.

Said nucleotide sequence is obtained by means of human intervention by modifying the nucleotide sequence that encodes original Etanercept sequence of SEQ ID NO: 3. The term "modification" means any chemical modification of the amino acid or nucleic acid sequence of the original Etanercept sequence.

The variant of the invention has reduced anti-hLTα activity compared with the original Etanercept molecule shown in SEQ ID NO: 3. Preferably, the variant of the invention is at least 60 times weaker as hLTα inhibitor than the original Etanercept molecule of SEQ ID NO: 3. "Anti-hLTα activity" is understood to be the reduction, blockage or inhibition of the hLTα activity in a cell.

The reduced anti-hLTα activity of the variant of the present invention can be determined by means of different types of assays known by the persons skilled in the art. It can be estimated, for example, but without limitation, by surface plasmon resonance analysis (SPR) to determine binding specificity and/or cytotoxicity assays to define biological activity, such as those shown in examples bellow.

The variant of the present invention has "reduced anti-hLTα activity" in comparison with the original Etanercept molecule of SEQ ID NO: 3 when it shows a significant decrease (applying statistical criteria) in its hLTα blocking activity with respect to the hLTα blocking activity of the original Etanercept molecule shown in SEQ ID NO: 3 used for the comparison.

The expression "to inhibit" or "to block" refers to reducing the activity level of the hTNF or hLTα protein, in a cell, in vivo or in vitro.

The variant of the invention binds hTNF and consequently the cell responses decreasing the hTNF activity.

Single amino acids in an amino acid sequence are represented herein as XN, where X is the amino acid in the sequence (designated by means of the one letter code universally accepted in amino acid nomenclature) and N is the position in the sequence. Amino acid substitutions are represented herein as $X_1NX_2$, where $X_1$ is the amino acid in the sequence of the non-mutated polypeptide, $X_2$ is the new amino acid in the sequence of the mutated polypeptide (variant) and N is the position in the amino acid sequence in relation to the positions of SEQ ID NO: 1.

Amino acid substitutions described herein introduced in the Etanercept original sequence can be obtained using genetic engineering techniques or recombinant DNA, such as for example by mutating the encoding sequence of the Etanercept original amino acid sequence by means of directed mutagenesis or they can be obtained by means of chemical synthesis of the nucleotide sequence which codes for the sequence of the variant of the invention that carries said amino acid substitutions.

Therefore, Etanercept variants of the invention can be synthesised, for example, but without limitations, in vitro. For example, by means of the synthesis of solid-phase polypeptides or recombinant DNA approaches. Variants of the invention can be produced in a recombinant manner, including their production as mature polypeptides or as pre-proteins that include a signal peptide. Thus, the polypeptide of the invention may further comprise a signal peptide in its N-terminal end, preferably the signal peptide shown in SEQ ID NO: 12.

Another aspect of the invention refers to an isolated polynucleotide, hereinafter "the polynucleotide of the invention", comprising a nucleic acid sequence encoding the polypeptide of the invention.

Due to the degeneration of the genetic code, various nucleotide sequences can encode the same amino acid sequence.

In accordance with the present invention, an isolated "nucleic acid molecule", "nucleotide sequence", "nucleic acid sequence" or "polynucleotide" is a nucleic acid molecule (polynucleotide) that has been eliminated from its natural medium (i.e. it has been subjected to human manipulation) and can include DNA, RNA or DNA or RNA derivatives, including cDNA. The nucleotide sequence of the present invention may or may not be chemically or biochemically modified and can be artificially obtained by means of cloning and selection methods or by means of sequencing.

The polynucleotide sequence of the invention can encode the mature polypeptide or a pre-protein consisting of a signal peptide linked to the mature polypeptide that must be subsequently processed.

The polynucleotide sequence of the present invention may also comprise other elements, such as introns, non-encoding sequences at ends 3' and/or 5', ribosome binding sites, etc. This nucleotide sequence can also include encoding sequences for additional amino acids that are useful for the purification or stability of the encoded polypeptide.

The polynucleotide sequence of the invention can be included in a gene or genetic construct, preferably in a recombinant expression vector. Said genetic construct may also comprise one or more gene expression-regulating sequences, such as promoters, terminators, enhancers, etc.

Thus, another aspect of the invention refers to a gene construct, hereinafter "the gene construct of the invention", comprising the polynucleotide of the invention. In a preferred embodiment, the gene construct of the invention is an expression vector, more preferably a viral vector, even more preferably a baculovirus.

The gene construct of the invention may further comprise a sequence encoding for a specifically cleavable linker peptide functionally interposed between the mutated ligand binding domain of TNFR2 (preferably, SEQ ID NO: 2) and the Fc portion of the IgG (preferably, SEQ ID NO: 11). Such a linker peptide may be, for instance, a peptide sensitive to thrombin cleavage, factor X cleavage or other peptidase cleavage.

The gene construct of the invention will generally be constructed such that the sequence encoding for the polypeptide of the invention is positioned adjacent to and under the control of an effective promoter. In certain cases, the promotor will comprise a prokaryotic promoter where the gene construct is adapted for expression in a prokaryotic host cell. In other cases, the promoter will comprise a eukaryotic promoter where the gene construct is adapted for expression in a eukaryotic host cell. In the later cases, the gene construct will typically further include a polyadenylation signal at position 3' of the carboxy-terminal amino acid, and within a transcriptional unit of the encoded polypeptide. Promoters of particular utility in the gene construct of the invention are mammalian promoters, cytomegalovirus promoters, baculovirus promoters or bacterial promoters, depending upon the cell used for the expression.

The expression "gene construct", "genetic construct" or "nucleic acid construct" as used herein relates to a functional unit required to transfer or express a nucleic acid sequence of interest, herein the nucleotide sequence of the invention as described, and regulatory sequences including, for example, a promoter, operably linked to the sequence that encodes the polypeptide, in an expression system. It refers to a nucleic acid molecule, mono or bicatenary, which is isolated from a natural gene or that is modified to contain nucleic acid segments in such a manner that they would otherwise not exist in nature.

The expression "nucleic acid construct" is synonymous to the expression "expression cassette" when the construct of nucleic acid contains the control sequences required for the expression of the encoding sequence.

The term "expression vector", also known as "expression construct" or "plasmid", relates to a DNA molecule, linear or circular, that comprises the nucleic acid sequence of the invention operably linked to additional segments that provide the transcription of the encoded polypeptide. Generally, a plasmid is used to introduce a specific nucleic acid sequence in a target cell. Once the expression vector is in the interior of the cell, the protein encoded by the nucleic acid sequence is produced by means of the ribosome complexes of the cellular transcription and translation machinery. The plasmid is often subject to engineering to contain regulatory sequences that act as enhancer and promoter regions that lead to an efficient transcription of the nucleic acid sequence carried on the expression vector. The objective of a well-designed expression vector is the production of large amounts of stable messenger RNA and, therefore, of proteins.

Expression vectors are basic tools for biotechnology and for the production of proteins, such as chimeric fusion proteins. The expression vector of the invention is introduced in a host cell such that the vector remains as a chromosome constituent or as an extra-chromosome self-replicating vector.

The term "expression" relates to the process whereby a polypeptide is synthesised from a polynucleotide. The term includes the transcription of the polynucleotide in a messenger RNA (mRNA) and the translation of said mRNA into a protein or polypeptide.

Examples of useful expression vectors are phages, cosmids, phagemids, yeast artificial chromosomes (YAC), bacterial artificial chromosomes (BAC), human artificial chromosomes (HAC) or viral vectors, such as adenovirus, baculovirus, retrovirus or lentivirus.

The variant of the invention can be prepared using any known means in the state of the art, such as the modification of a DNA sequence that encodes the original Etanercept sequence of SEQ ID NO: 3, transformation of the modified DNA sequence in an adequate host cell and the expression of the modified DNA sequence to obtain the Etanercept variant.

Another aspect of the invention refers to a host cell, hereinafter "the host cell of the invention" or "the cell of the invention", comprising the polypeptide, the polynucleotide or the gene construct of the invention.

The host cell of the invention may be either a eukaryotic or a prokaryotic host cell. A host cell is the recipient of an expression vector, cloning vector or any other DNA molecule. Therefore, it includes any cultivable cell that may be modified through the introduction of DNA not contained naturally therein. Preferably, a host cell is that in which the polynucleotide of the invention may be expressed, giving rise to a stable polypeptide, post-translationally modified and located in the appropriate subcellular compartment.

The election of an appropriate host cell may also be influenced by the election of the detection signal. For example, the use of constructs with reporter genes (for example, lacZ, luciferase, thymidine kinase or green fluorescent protein "GFP") can provide a signal selectable through the activation or inhibition of the transcription of the nucleotide sequence of interest in response to a transcription-regulating protein. In order to achieve optimum selection or screening, the phenotype of the host cell must be considered.

For instance, when used in combination with a baculovirus promoter, the insect cell lines Hi5, SF9 or SF21 may be used as host cells. S2 cells from *Drosophila melanogaster* could also be used. In any case, the polynucleotide or the gene construct of the invention encoding the polypeptide of the invention is placed under the transcriptional control of regulatory signals functional in the host cell. Said regulatory signals appropriately control the expression of the polypeptide of the invention to allow any necessary transcriptional and post transcriptional modification.

Preferably, the host cell of the invention is a mammalian host cell.

Preferably, the host cell of the invention is a Hi5, HEK293 or CHO-K1 cell or their derivatives, more preferably it is a HEK293 or CHO-K1 cell.

Another aspect of the invention relates to the use of the host cell of the invention to obtain the polypeptide of the invention.

The host cell of the invention may be cultivated for such purpose. A host cell culture relates to the in vitro process of maintaining and growing host cells. Cell cultures need controlled conditions of temperature, pH, percentages of gases (oxygen and carbon dioxide), in addition to the presence of the adequate nutrients to allow cellular viability and division. The skill in the art will know which conditions must be applied to the cell culture depending on the requirements of the selected host cell. Cell cultures can be carried out in solid substrates such as agar or in a liquid medium, which enables the expansion of large amounts of cells in suspension.

Once the cell of the invention has been cultivated and the variant of the invention has been expressed, it can be purified. The term "to purify", as used in the description, relates to the isolation of the variant of the invention from the other polypeptides present in the culture medium in which the host cell of the invention has grown. The isolation of the variant can be carried out using differential solubility techniques, chromatography, electrophoresis or isoelectric focusing. Chromatography techniques can be based on molecular weight, ion charge (based on the ionisation state of the amino acids under working conditions), the affinity of the protein for certain matrixes or chromatographic columns, or by means of purification tags, and can be carried out on a column, on paper or on a plate. The isolation of the protein can be carried out, for example, by means of precipitation with ammonium sulphate, fast protein liquid chromatography (FPLC) or high performance liquid chromatography (HPLC), using automated systems that significantly reduce purification time and increase purification efficiency.

Another aspect of the invention refers to the use of the polypeptide of the invention for binding chemokines and their analogues, preferably TNF, more preferably hTNF. This aspect of the invention encompasses an in vitro use, for instance with the aim of in vitro detecting the presence or activity of chemokines (preferably hTNF). Thus, the polypeptide of the invention may be included in a kit for the in vivo or in vitro, preferably in vitro, detection of chemokines activity or presence, preferably hTNF activity or presence.

Another aspect of the invention refers to the use of the polypeptide of the invention for blocking binding of chemokines, preferably hTNF, to their corresponding cell surface receptors, preferably TNFR2, and/or for modulate, preferably for inhibit, chemokine, preferably hTNF, biological activity, more preferably, in vivo.

Another aspect of the invention refers to a pharmaceutical composition, hereinafter "the composition of the invention", comprising the polypeptide of the invention, preferably the polypeptide of the invention comprising, more preferably consisting of, SEQ ID NO: 4.

This composition of the invention comprises the variant of the invention in a therapeutically effective amount. A "therapeutically effective amount" is understood to be the amount of variant of the invention that, when administered to the patient, produces the desired effect, thereby neutralizing the hTNF inflammatory activity and with reduced blocking effect over hLTα compared with the original Etanercept molecule. The therapeutically effective amount may vary depending on a variety of factors, for example, but not limited to, the type of autoimmune or inflammatory condition and its severity, as well as age, weight, sex, physical condition, response or tolerance, etc., of the individual to whom the composition of the invention is going to be administered. More preferably, the therapeutically effective amount of the variant of the invention in the composition of the invention is in a range between 10 and 50 mg, preferably 25 mg or 50 mg.

In a more preferred embodiment, the composition of the invention further comprises a pharmaceutically acceptable vehicle or excipient, adjuvant and/or other active ingredient.

The "pharmaceutically acceptable excipients or vehicles" that may be used in the composition of the invention are those known by the persons skilled in the art.

The term "excipient" makes reference to a substance which aids the absorption of the elements of the composition of the invention, stabilises said elements, activates or helps to prepare the composition in the sense of giving it consistency. Therefore, excipients may have a bonding function for keeping the ingredients bonded together, such as for example in the case of starches, sugars or celluloses, a dyeing function, a protective function for protecting the composition, such as for example to isolate it from the air and/or humidity, a filling function for filling a pill, capsule or any other form of presentation, such as for example in the case of dibasic calcium phosphate, a disintegrating function to facilitate the dissolution of the components and their absorption, not excluding other types of excipients not mentioned in this paragraph.

The "pharmaceutically acceptable vehicle", like the excipient, is a substance or combination of substances used in the composition to dilute any of the components comprised therein up to a certain volume or weight. The term "vehicle" refers to a solvent, coadjuvant, excipient or carrier with which the composition of the invention must be administered; obviously, said vehicle must be compatible with the other components of said composition. Pharmaceutically acceptable vehicles may be, but not limited to, solids, liquids, solvents or surfactants. Examples of vehicles may be, but not limited to, water, oils or surfactants, including those of petroleum, animal, vegetable or synthetic origin, such as for example, in the non-limiting sense, peanut oil, soybean oil, mineral oil, sesame seed oil, castor oil, polysorbates, sorbitan esters, ether sulfates, sulfates, betains, glucosides, maltosides, fatty alcohols, nonoxinoles, poloxamers, polioxiethylenes, poliethylenglycols, dextrose, glycerol, digitonin and similar. The pharmaceutically acceptable vehicle is an inert substance or vehicle having an action similar to any of the elements comprised in the composition of the present invention. The function of the vehicle is to facilitate the incorporation of other elements, enable better dosing and administration or give consistency and format to the composition. When the format of the presentation is liquid, the pharmacologically acceptable vehicle is the solvent.

The composition of the invention may be administered in combination with one or more immunosuppressant and/or anti-inflammatory substances, agents, drugs, compounds or compositions. In particular, the composition of the invention may be administered with other substances for the treatment of rheumatoid arthritis. These substances may or may not be included within the composition of the invention together with the polypeptide of the invention. The administration of these combinations may be simultaneous or sequential with the polypeptide of the invention.

Thus, the composition of the invention may comprise other active ingredients such as immunosuppressant and/or anti-inflammatory substances. For instance, but without limitation, it may comprise methotrexate, glucocorticoids, salicylates, non-steroidal anti-inflammatory drugs, and/or analgesics, which may be administered during or with the treatment with the polypeptide of the invention.

The composition of the invention and/or its formulations may be administered in a variety of ways including, but not limited to, parenteral, intraperitoneal, topic, intravenous, intradermal, epidural, intraspinal, intrastromal, intraarticular, intrasinovial, intratecal, intralesional, intraarterial, intracardiac, intramuscular, intranasal, intracranial, cutaneous or subcutaneous, intraorbital, intracapsular, ophthalmological or ocular, percutaneous, surgical implant, internal surgical paint, infusion pump or via catheter. Preferably, the composition of the invention is formulated for subcutaneous administration.

The composition of the present invention is also suitable for being applied by means of medical devices which make it possible to release the active ingredient(s) (polypeptide of the invention) in adequate concentrations for treating autoimmune and inflammatory conditions based on TNF activity. These devices must be, preferably, appropriate for locally administering the active ingredient(s), allowing the treatment to act on the affected region and not be dispersed. The devices can, for example, but not limited to, include the active ingredient(s) in their interior or be coated therewith.

The composition of the present invention can be formulated for its administration to an animal, preferably a mammal, including humans, in a variety of ways known in the state of the art. Examples of preparations could include semi-solid (ointment, cream, balm, gel, hydrogel, foam, lotion, soap, gelatin, etc.) or liquid (aqueous or non-aqueous solutions, hydroalcoholic or hydroglycolic solutions, suspensions, emulsions, syrups, anhydrous compositions, aqueous dispersions, oils, milks, balsams, liniments, serums, etc.) preparations, preferably for subcutaneous administration. The composition of the present invention may also be in the form of sustained release formulations or any other conventional release system. The term "sustained release" is used in reference to a compound vehiculisation system that enables the gradual release of said compound during a period of time and preferably, although not necessarily, with relatively constant compound release levels over a period of time. Illustrative examples of sustained release vehicles or systems include, but are not limited to, liposomes, mixed liposomes, oleosomes, niosomes, etosomes, milicapsules, microcapsules, nanocapsules, sponges, cyclodextrins, blisters, micelles, mixed surfactant micelles, mixed surfactant phospholipid micelles, milispheres, microspheres, nanospheres, lipospheres, microemulsions, nanoemulsions, miniparticles, miliparticles, microparticles, nanoparticles, solid lipid nanoparticles, nanostructured lipid media, polymeric materials, biodegradable or non-biodegradable patches or implants, or biodegradable microparticles, such as for example biodegradable microspheres.

In another preferred embodiment, the pharmaceutical composition of the invention is in powder form, more preferably powder included within vials.

The composition of the invention may also comprise an autoinjector, syringe, pen or any other device for the injectable, preferably subcutaneous, administration of the polypeptide of the invention to the patient to be treated. A therapeutically effective amount of the polypeptide of the invention may be included within these devices or they may be provided separately within the composition of the invention.

The composition of the invention is, preferably, administered once or twice a week.

Another aspect of the invention refers to the polypeptide or variant, polynucleotide, or gene construct of the invention for use as a medicament. Alternatively, this aspect of the invention refers to the use of the polypeptide or variant, polynucleotide, or gene construct of the invention for the manufacture of a medicament.

The term "medicament" or "drug" makes reference to any substance used to prevent, alleviate, treat or cure diseases, conditions or pathologies, preferably those in which an exacerbated TNF activity, more preferably hTNF activity, is involved, in humans, or in any other animal.

In the context of the present invention, the term "medicament" relates to a preparation that comprises the polypeptide or variant, polynucleotide, or gene construct of the invention; preferably the variant of the invention, more preferably the variant of the invention comprising, even more preferably consisting of, SEQ ID NO: 4.

The medicament to which the present invention refers may be for human or veterinary use. The "medicament for human use" is any substance or combination of substances that have the properties for treating or preventing diseases in human beings or that can be used in human beings or administered to humans for the purpose of restoring, correcting or modifying physiological functions by exercising a pharmacological, immunological or metabolic action. The "medicament for veterinary use" is any substance or combination of substances having curative or preventive properties with respect to animal diseases or conditions or that can be administered to the animal in order to restore, correct or modify its physiological functions by exercising a pharmacological, immunological or metabolic action.

The medicament referred to in the present invention may be used together with other active ingredients or therapies in the manner of a combined therapy. The other active ingredients may form part of the same composition or can be provided by means of a different composition, being administered at the same time or at different times (simultaneous or sequential administration).

Another aspect of the invention refers to the polypeptide or variant, polynucleotide, or gene construct of the invention for use in the treatment of an autoimmune or inflammatory disease. Alternatively, this aspect of the invention refers to the use of the polypeptide or variant, polynucleotide, or gene construct of the invention for the manufacture of a medicament for the treatment of an autoimmune or inflammatory disease.

The term "treatment", as understood in the present invention, refers to combating the effects caused as a result of the disease or pathological condition of interest in an individual (preferably a mammal and, more preferably, a human) which includes:

(i) inhibiting the disease or pathological condition, i.e. interrupting its course;

(ii) alleviating the disease or pathological condition, i.e. causing the regression of the disease or pathological condition or its symptoms;

(iii) stabilising the disease or pathological condition.

The term "prevention", as understood in the present invention, consists of avoiding the appearance of the disease or pathological condition in an individual (preferably a mammal and, more preferably, a human), particularly when said individual is susceptible of developing the disease or pathological condition but has not been diagnosed yet.

Preferably, the autoimmune or inflammatory disease is a disease or condition mediated by hTNF or in which an exacerbated hTNF activity is involved.

In a more preferred embodiment, the disease is a TNF-dependent inflammatory disease.

A "TNF-dependent inflammatory disease" is any disease or condition that occurs with inflammation and in which hTNF is involved or in which an exacerbated TNF activity exists. Chronic inflammatory conditions are encompassed within this definition.

In a more preferred embodiment, the disease is a rheumatic disorder.

"Rheumatic disorder" or "rheumatism" is a term that encompasses conditions causing chronic, often intermittent, pain affecting the joints and/or connective tissue. Major rheumatic disorders include, but without limitation, back pain, bursitis, tendinitis, capsulitis, neck pain, osteoarthritis, palindromic rheumatism, rheumatoid arthritis, ankylosing spondylitis, relapsing polychondritis, systemic lupus erythematosus, gout, inflammatory arthritis, pseudogout, juvenile rheumatoid arthritis, Sjögren syndrome, scleroderma, polymyositis, dermatomyositis, Behçet's disease, or psoriatic arthritis.

In an even more preferred embodiment, the disease is selected from the list consisting of: rheumatoid arthritis (moderate or severe) including juvenile rheumatoid arthritis (moderate or severe) and juvenile idiopathic arthritis, Crohn's disease, psoriasis (preferably, psoriatic arthritis or plaque psoriasis), ankylosing spondylitis, multiple sclerosis or inflammatory bowel disease.

In a particular embodiment, the medicament of the invention is used for:

reducing signs and symptoms, inducing major clinical response, inhibiting the progression of structural damage and improving physical function in patients with moderately to severely active rheumatoid arthritis (RA), reducing signs and symptoms of moderately to severely active polyarticular course juvenile rheumatoid arthritis (JRA) or juvenile idiopathic arthritis (JIA) in patients who have had an inadequate response to one or more antirheumatic drugs, the treatment of chronic moderate to severe plaque psoriasis in patients who are candidates for systemic therapy or phototherapy, the treatment of signs and symptoms of active psoriatic arthritis, to improve physical function, and to prevent the progression of structural damage, and/or the treatment of the signs and symptoms of spondylitis, such as active ankylosing spondylitis, in adults or for the treatment of juvenile spondyloarthropathy in pediatric patients.

Unless otherwise defined, all technical and scientific terms used herein have the same meaning as commonly understood by one of ordinary skilled in the art to which this invention belongs. Methods and materials similar or equivalent to those described herein can be used in the practice of the present invention. Throughout the description and claims the word "comprise" and its variations are not intended to exclude other technical features, additives, components, or steps. Additional objects, advantages and features of the invention will become apparent to those skilled in the art upon examination of the description or may be learned by practice of the invention. The following examples, drawings and sequence listing are provided by way of illustration and are not intended to be limiting of the present invention.

EXAMPLES

Figure 1:
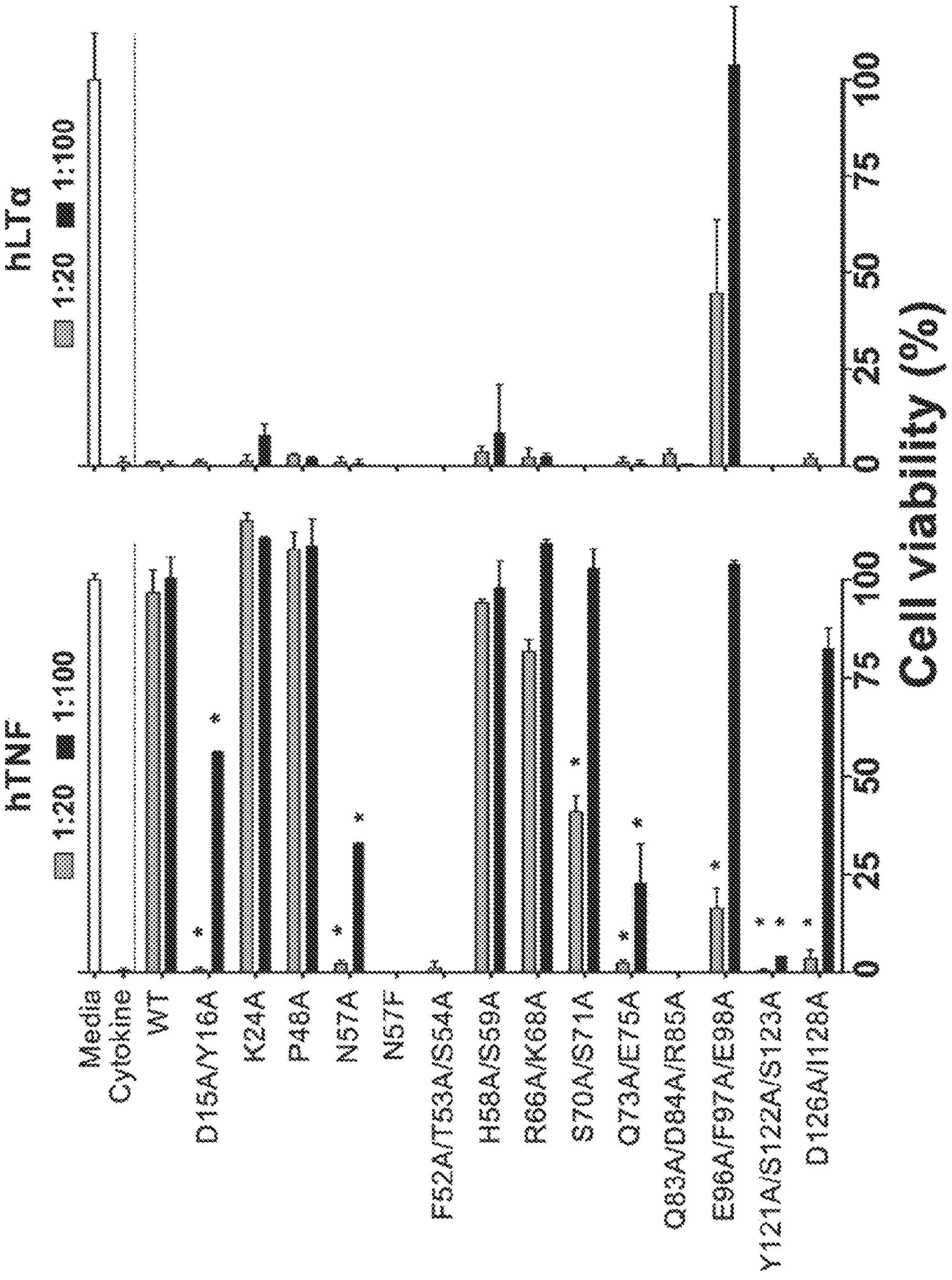
FIG. 1. An EFE motif in the 90 s loop of CrmD abrogates its anti-hLTα activity. A cytotoxic dose of hTNF and hLTα was incubated with L929 cells in the absence or presence of CrmD wild-type (WT) or the indicated mutants at increasing cytokine:protein molar ratios (legend above each graph). After 18 h cell survival was assessed as the A490 determined using Cell Titer Aqueous One Solution Kit. Data are represented as the % relative to the A490 recorded for cells incubated without cytokine (Media, 100% viability). The corresponding effector cytokine is indicated above each graph. Results are shown as mean±SD of triplicates of three representative experiments. Asterisks indicate mutants that display significantly different viability values compared to CrmD WT at the same protein dose (*$p<0.05$, ANOVA with Bonferroni multiple comparison test).

Example 1. Transfer of the EFE Motif of CrmD into the 90 s Loop of Etanercept Specifically Impair its Anti-hLTα Activity The inflammatory diseases currently treated with Etanercept are predominantly TNF-driven. Therefore, the anti-hLTα activity of Etanercept not only appears to be clinically unnecessary but it could also pose a source of unwanted complications. It has been identified in this invention that a 90 s loop EFE motif in the soluble viral TNF decoy receptor termed CrmD specifically hinders its anti-hLTα activity. Unlike CrmD wild-type, a CrmD E96A/F97A/E98A mutant is able to inhibit the cytotoxic activity of hLTα (FIG. 1). Then, it was here hypothesized that by transferring the EFE motif of CrmD into the 90 s loop of Etanercept, we could disrupt its anti-hLTα activity while keeping it active against hTNF.

Figure 2A:
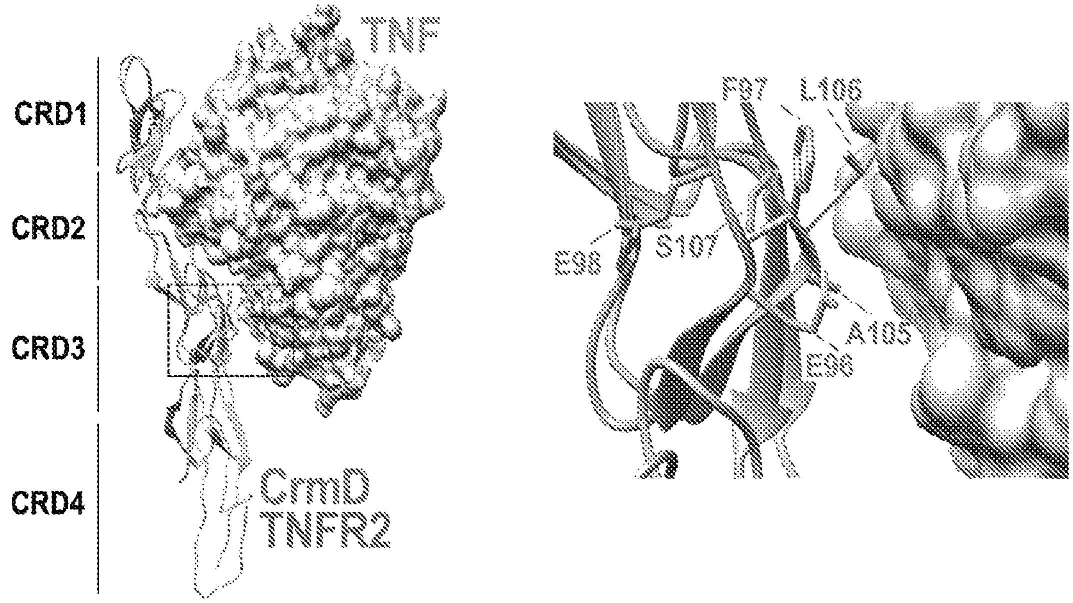
FIGS. 2A-2B. Etanercept A105E/L106F mutant displays enhanced TNF neutralizing specificity. A) Localization of the side chains of the EFE motif in the 90 s loop of CrmD. CrmD three-dimensional folding was modeled using I-TASSER (Yang J., Yan T., Roy A. et al., 2015, Nat. Methods, 12, 7-8) and aligned with the crystallographic structure of the TNFR2-TNF structure (PDB: 3ALQ) (left panel) in Chimera. In the right panel, magnification of the 90 s loop region (dashed frame) showing the side chains of the overlapping EFE and ALS motifs of CrmD and TNFR2, respectively. B) hTNF- and hLTα-mediated cytotoxicity assays. L929 cells were incubated with 1.2 nM of the corresponding cytokine, as labeled above each graph, with increasing concentrations of wild type (WT), L106F or A105E/L106F Etanercept. After 18 h, cell viability was assessed as the A490 detected using Cell Titer Aqueous One Solution Kit. Data are represented as the % relative to the A490 recorded for cells incubated without cytokine (100% cell viability). Mean±SD of triplicates from two independent experiments are shown. The horizontal line above the hTNF graph indicates the Etanercept concentrations in which statistically significant differences were detected between the anti-hTNF activity of the WT and the A105E/L106F mutant (*$p<0.05$, two-tailed t test).

An amino acid sequence alignment showed that the EFE motif ($Glu^{96}$-$Phe^{97}$-$Glu^{98}$) in the CRD3 of CrmD aligns with an ALS motif ($Ala^{105}$-$Leu^{106}$-$Ser^{107}$) in the 90 s loop of human TNFR2, which corresponds to the TNF-binding moiety of Etanercept. Furthermore, it was observed that in the crystal structure of the TNFR2:TNF complex (PDB: 3ALQ), the TNFR2 $Ser^{107}$ was not facing to the ligand (FIG. 2A). Similarly, the structural superimposition of a CrmD model with the structure of TNFR2 suggested that the third amino acid of this motif in CrmD, $Glu^{98}$, would also be far from the ligand interface. Thus, to introduce the lowest number of modifications into the original sequence of Etanercept, we mutated only the TNFR2 $Ala^{105}$ and $Leu^{106}$ to their equivalent amino acids in the 90 s loop of CrmD (Glu (E) and Phe (F)). The WT (non-mutant or original Etanercept) and the L106F and A105E/L106F forms of Etanercept were expressed in a baculovirus system and purified by affinity chromatography.

hTNF and hLTα binding affinity of wild type (WT), L106F and A105E/L106F Etanercept was calculated by SPR. The kinetic affinity constants, association (Ka), dissociation (Kd) and binding affinity ($K_D$), and their standard errors (SE), are shown for each interaction. SPR analysis revealed that the hTNF and hLTα binding affinities of Etanercept were not significantly affected in the mutants (Table 1).

TABLE 1

| Ligand | Etanercept | (Ka ± SE) × $10^{+5}$ (1/Ms) | (Kd ± SE) × $10^{-3}$ (1/s) | $K_D$ (nM) |
|---|---|---|---|---|
| hTNF | WT | 28.00 ± 0.67 | 0.79 ± 0.01 | 0.28 |
| | A105E/L106F | 30.07 ± 0.56 | 2.10 ± 0.03 | 0.69 |
| | L106F | 30.00 ± 0.85 | 2.01 ± 0.05 | 0.67 |
| hTLα | WT | 8.85 ± 0.54 | 3.49 ± 0.21 | 3.95 |
| | A105E/L106F | 2.37 ± 0.05 | 1.69 ± 0.07 | 7.13 |
| | L106F | 4.64 ± 0.03 | 1.20 ± 0.01 | 2.59 |

Figure 2B:
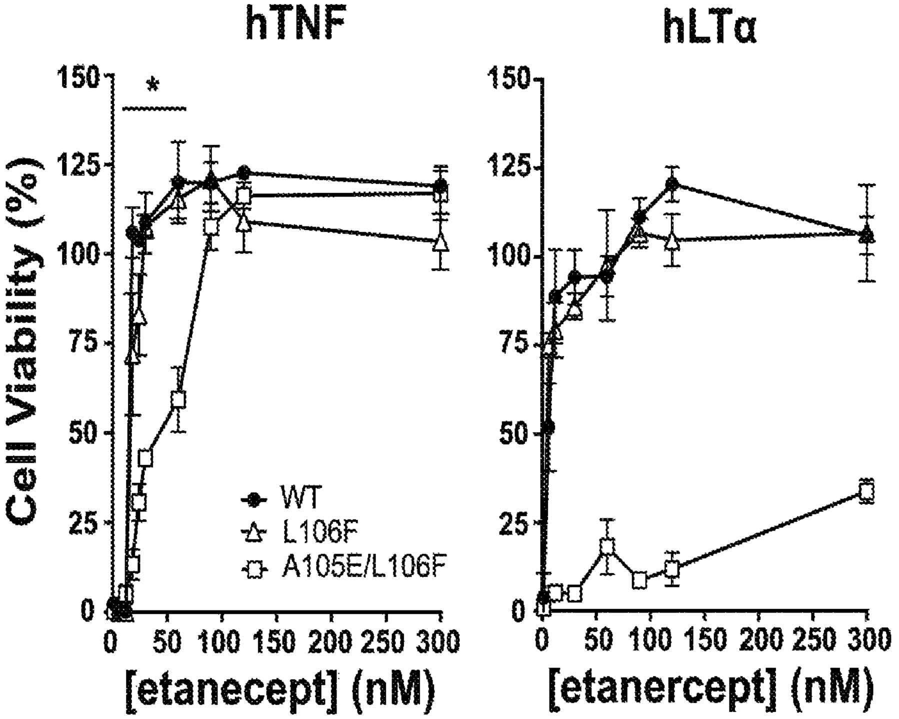

However, binding affinity does not always correlate with neutralizing potency. Therefore, the capacity of A105E/L106F, L106F and WT Etanercept to block the cytotoxic activity of hTNF and hLTα on L929 cells was compared. As shown in FIG. 2B, 20 nM of Etanercept WT was enough to fully neutralize both hTNF and hLTα (FIG. 2B), reaching 50% cell viability at 10-20 nM and 5 nM (EC50), respectively. The anti-hTNF and anti-hLTα activities of the mutant L106F were comparable to those of WT Etanercept. On the other hand, the A105E/L106F mutant protected 50% of the cells from hTNF at 30-60 nM and reached full protection at 90 nM (FIG. 2B). In contrast, this double mutant showed a very low anti-hLTα activity and required a high 300 nM dose to protect only 35% of the cells from this cytokine (FIG. 2B), positioning its anti-hLTα EC50 at even higher concentrations. Therefore, the A105E/L106F variant was at least 60× weaker as hLTα inhibitor.

It has been demonstrated herein that the anti-hLTα activity of Etanercept can be vastly hampered by making its 90 s loop look more like that of CrmD in a A105E/L106F Etanercept mutant. The slight defect observed in the anti-hTNF activity of this mutant could be potentially overcome in the clinic by a small dose increase without compromising hLTα-mediated immune functions.

Therefore, this A105E/L106F variant could set the foundation for a safer second generation of Etanercept featuring the benefits of a soluble decoy receptor and the high TNF specificity of the antibody therapy.

Example 2. Materials and Methods

Cells and Reagents

L929 cells (ATCC, Manassas, VA) were grown in DMEM supplemented with 10% FCS.

Recombinant baculoviruses were generated and amplified in adherent Hi5 insect cells cultured in TC-100 medium supplemented with 10% FCS and 1× non-essential amino acids. Suspension Hi5 cells maintained in Express Five (Life Technologies, Carlsbad, CA) medium supplemented with 8 mM L-glutamine were used for the expression of the recombinant protein.

Recombinant cytokines were purchased from R&D Systems (Minneapolis, MN) and reconstituted and stored following the manufacturer's recommendations.

Construction of Recombinant Baculovirus

All the proteins described in this study were expressed by recombinant baculoviruses. The ECTV strain Hampstead CrmD coding sequence was extracted by PCR from a pBAC1 (Life Technologies) derived plasmid termed pMS1 (Saraiva M., Alcami A., 2001, J. Virol., 75, 226-233) using the primers Crm34 (5'-gcgggatccgatgttccgtatacacccat-taatggg-3', SEQ ID NO: 5) and CrmD33 (5'-gcgctcgagg-catctctttcacaatcatttgg-3', SEQ ID NO: 6). The CrmD gene lacking the signal peptide (residues 21-320) was cloned into pAL7 (Montanuy I., Alejo A., Alcami A., 2011, FASEB J., 25, 1960-1971), a modified pFastBac1 vector, in frame with a N-terminal honeybee melittin signal peptide and a C-terminal V5-6×His tag. The resulting plasmid was termed pSP3.

The CrmD point mutants were generated using the QuikChange II site-directed mutagenesis kit (Agilent Technologies, Santa Clara, CA). For this, pSP3 was used as template for PCR reactions with the corresponding pair of primers for each mutation. The Etanercept L106F and A105E/L106F mutants were generated using the primer pairs, RM6mut2F (5'-gctggtactgcgcgttcagcaagcaggaggg-3', SEQ ID NO: 7) and RM6mut2R (5'-ccctcctgcttgct-gaacgcgcagtaccagc-3', SEQ ID NO: 8), and RM6mut3F (5'-cggctggtactgcgagttcagcaagcaggaggg-3', SEQ ID NO: 9) and RM6mut3R (5'-ccctcctgcttgctgaactcgcagtaccagccg-3', SEQ ID NO: 10), respectively.

pRM6 is a pFastBac1-based plasmid containing the wild-type form of a Fc fusion protein of the TNF binding domain of TNFR2, known in the clinic as Etanercept (Pontejo, S. M., Alejo, A., Alcami, A., 2015, J Biol Chem 290, 15973-15984). Mutagenesis was confirmed by sequencing.

The plasmids described above were used to generate recombinant baculoviruses using the Bac-to-Bac system (Life Technologies) following the manufacturer's instructions.

Subsequently, viral stocks were amplified by infecting adherent Hi5 cells at low multiplicity of infection (0.1-0.01 pfu/cell).

Protein Expression and Purification

Hi5 suspension cells were infected with the corresponding recombinant baculovirus at high multiplicity of infection (2 pfu/cell). Supernatants were harvested 3 days after infection, clarified at 6,000×g for 40 min and then concentrated to 2.5 ml in a Stirred Ultrafiltration Cell 8200 (Millipore, Burlington, MA). The concentrate was desalted and buffer was exchanged to 0.1 M phosphate buffer containing 300 mM NaCl and 10 mM imidazole using PD-10 desalting columns (GE Healthcare, Chicago, IL).

His-tagged CrmD proteins were purified by metal chelate affinity chromatography (Ni-NTA resin, Qiagen, Germantown MD). Etanercept (TNFR2-Fc) proteins were purified using protein A-coupled sepharose columns (Sigma, St. Louis, MO). Protein containing fractions were pooled, concentrated and dialyzed in PBS. Final protein concentration was calculated by gel densitometry.

Cytotoxicity Assays

The ability of CrmD, Etanercept and their mutants to inhibit TNF superfamily ligands (TNFSF) was tested by cytotoxicity assays on L929 cells as previously described (Pontejo, S. M., Alejo, A., Alcami, A., 2015, J Biol Chem 290, 15973-15984). Briefly, 20 ng/ml of hTNF and hLTα were incubated for 1 h at 37° C. in the presence of increasing amounts of recombinant protein. Subsequently, the cytokine-protein mixtures were added to L929 cells seeded at 12,000 cells/well in 96-well plates in the presence of 4 μg/ml of actynomicyn D (Sigma). Cell viability was assessed after 18 h using Cell Titer Aqueous One Solution Kit (Promega, Madison, WI) following the manufacturer's instructions and the absorbance at 490 nm (A490) was determined in a Sunrise microplate reader (Tecan, Mannedorf, Switzerland). The A490 of all samples was normalized with the A490 of cells incubated only with the cytokine (0% viability). Cell viability for each sample was calculated in reference to the A490 obtained in wells where cells were incubated without cytokine ("media", 100% viability).

Surface Plasmon Resonance (SPR) Assays

The ligand binding properties of recombinant proteins were characterized by SPR using a Biacore X biosensor (GE Healthcare). For determination of kinetic affinity constants, recombinant proteins were immobilized on CM4 chips at low density (≈500 RU).

Increasing concentrations of TNFSF cytokines were injected in HBS-EP buffer at 30 μl/min during 2 min and a 5-min dissociation was recorded. A 0.1-1000 nM concentration range of analyte was typically used. Between analyte injections, the chip surface was regenerated with 10 mM glycine-HCl pH 2.0. Kinetic data were globally fitted to a 1:1 Langmuir model using the Biaevaluation 3.2 software. Bulk refractive index changes were removed by subtracting the responses recorded in the reference flow cell, and the response of a buffer injection was subtracted from all sensorgrams to remove systematic artifacts. The average KD of 10 fittings containing sensorgrams for at least 6 different analyte concentrations from at least two independent experiments was calculated. The fitting providing the closest KD to the average KD was chosen to represent the kinetic affinity constants of each interaction.

The invention claimed is:

1. An isolated polypeptide comprising a variant of the amino acid sequence of SEQ ID NO: 1, wherein the variant is selected from the group consisting of the amino acid substitution A105E, the amino acid substitution L106F, and the amino acid substitutions A105E and L106F in the sequence of SEQ ID NO: 1.

2. The isolated polypeptide according to claim 1, wherein the variant comprises the amino acid substitution L106F in the sequence of SEQ ID NO: 1.

3. The isolated polypeptide according to claim 1, wherein the variant comprises the amino acid substitutions A105E and L106F in the sequence of SEQ ID NO: 1.

4. The isolated polypeptide according to claim 1, linked to the Fc fragment of a human IgG1.

5. The isolated polypeptide according to claim 1, comprising the amino acid sequence of SEQ ID NO: 4.

6. A pharmaceutical composition comprising the isolated polypeptide according to claim 1.

7. The pharmaceutical composition according to claim 6, formulated for subcutaneous administration.

8. An isolated polynucleotide comprising a nucleic acid sequence encoding the isolated polypeptide according to claim 1.

9. A gene construct comprising the isolated polynucleotide according to claim 8.

10. A host cell comprising the isolated polynucleotide according to claim 8.

11. A gene construct comprising the isolated polynucleotide according to claim 8, wherein said gene construct is a viral vector.

* * * * *